United States Patent [19]

Stocton et al.

[11] Patent Number: 4,796,696
[45] Date of Patent: Jan. 10, 1989

[54] DEVICE FOR HEATING OR COOLING INFUSION FLUIDS OR INJECTABLE FLUIDS

[75] Inventors: Paul M. Stocton, Dallas, Tex.; Michael Greive, Senden-Ottmarsbocholt; Raymond Glocker, Munster-Hiltrup, both of Fed. Rep. of Germany

[73] Assignee: Glocker und Greive GmbH, Fed. Rep. of Germany

[21] Appl. No.: 881,103

[22] Filed: Jul. 2, 1986

[51] Int. Cl.$^4$ .............................. F28F 3/12; A61F 7/12
[52] U.S. Cl. ..................................... 165/169; 128/401; 604/257
[58] Field of Search ................. 165/169; 62/398, 394, 62/400, 397, 396, 464; 604/7, 8, 257; 128/400, 401

[56] References Cited

U.S. PATENT DOCUMENTS

| | | | |
|---|---|---|---|
| 1,372,135 | 3/1921 | Green | 62/398 |
| 2,035,213 | 3/1936 | Anderson | 165/169 |
| 2,449,343 | 9/1948 | Torbensen | 165/169 X |
| 3,601,384 | 8/1971 | Durdin | 165/169 X |
| 4,111,209 | 9/1978 | Wolvek et al. | 128/400 |
| 4,204,613 | 5/1980 | Terzian et al. | 165/169 X |
| 4,407,356 | 10/1983 | Delau | 165/169 X |

FOREIGN PATENT DOCUMENTS

| | | | |
|---|---|---|---|
| 544688 | 2/1932 | Fed. Rep. of Germany | 164/167 |
| 539529 | 9/1941 | United Kingdom | 165/169 |

*Primary Examiner*—Ira S. Lazarus
*Assistant Examiner*—Richard R. Cole
*Attorney, Agent, or Firm*—Thomas L. Cantrell

[57] ABSTRACT

Device for heating or cooling infusion fluids or injectable fluids comprising a heat exchanger in the form of a hollow cylindrical or truncated, conical, double cased pot, open at the top; the outer wall being higher than the inner wall of the double casing, wherein the hollow space of the casing is sealed by a ledge surrounding the upper brim of the inner wall and extending up to the outer wall whereby the ledge is provided with connection branches spaced apart from each other and extending into the interior of the pot, where two parallel ridges form a double helix respectively a double thread within the whole of the hollow space of the casing between the walls, wherein each of the ends of the double helix is connected to one of the connection branches and the return of the double helix is located close to the bottom of the pot as a semi-circular arch.

9 Claims, 2 Drawing Sheets

DEVICE FOR HEATING OR COOLING INFUSION FLUIDS OR INJECTABLE FLUIDS

The invention refers to a device for heating or cooling of infusion fluids or injectable fluids, especially to the structure of a heat-exchanger.

U.S. Pat. No. 4,111,209 of S. Wolvek, B. L. Hanson and D. Bregman refers to an apparatus for adjusting the temperature of a fluid and a method of heating or cooling of organs or regions within the human body by said fluid. The heat-exchanger is provided as a coil located at the bottom of a pot. The terminal ends of the cooling coil are provided at the upper portion of the pot and extending outward through the pot wall and are provided with fittings for tubes. For the purpose of cooling the interior of the pot is for example filled with ice water so that the cooling coil is in direct contact with the cooling medium and a fluid passing through the interior of the coil is cooled during its passage.

U.S. Pat. No. 3,100,487 of L. N. Bathish relates to an apparatus for administering medical liquids having the form of an open plastic pot. During storage a coil is positioned adjacent to the bottom of the pot and a removable card is provided above the coil to protect the flexible coil during storage. The end of the coil can be provided with a tip for the direct administering of tho dripping fluid or as a structure being connectable with such a tip. In use the coil is removed from the interior of the pot and the other end of the coil is connected with a connector at the outer surface of the pot. A fluid introduced into the pot can be supplied to the desired place through the inner wall of the connector. During storage the pots, being fitted into one another are positioned within a sterilizable bag.

The disadvantage of the known apparatuses is that they are expensive to produce and that they are not immediately manufactured ready for use.

It is the object of the invention to provide a device for the heating or cooling of in-fusion fluids or injectable fluids which is inexpensive in production and which needs only simple measures to be ready for use and to which the catheters needed in use can already be attached. The term 'ready for use' means that the whole device is sterilisable and can be stored maintaining the portions sterile which are needed in said condition during use.

The object of the invention is solved by a device for heating or cooling infusion fluids or injectable fluids comprising a heat exchanger in the form of a hollow cylindrical truncated conical pot which is open at the top. The pot has a double casing and the outer wall of the pot is higher than the inner wall of the double casing, whereby the hollow space of the casing is sealed by a ledge surrounding the brim of the inner wall and extending outward up to the outer wall and the ledge is provided with two connection branches spaced apart from each other and extending within the inner space of the pot.

Vertical guiding bars can be positioned within the hollow space of the casing between the walls, around its circumference, and being alternatively at a distance from the bottom and the top of the hollow space respectively, in order to extend the distance the fluid to be cooled travels within the hollow space of the casing. The connection branches are positioned at each side and spaced apart from a guiding bar extending from the bottom to the top of the hollow space of the casing. The extension of the flow can also be realized by arranging two parallel ridges in the form of a double helix, forming a double thread, occupying the hollow space of the casing between the walls wherein each of the ends of the double helix is connected to one of the connection branches and the return path of the double helix is located close to the bottom of the pot as a semi-circular arch. Said semi-circular arch provides a connection between both courses of the double-thread.

In order to simplify preparation and assembling of the double casing a preferred embodiment of the invention provides the inner wall of the double casing as a pot having a ledge at the brim and a rim at the lower pot edge as well as the ridges, each projecting from the outer surface to such an extent that they fit firmly into the inner surface to the outer wall. It is preferred that the connection branches protrude from the ledge and extend into the hollow space of the casing to each of the termination portions of the double helix or in the interspace between two vertical guiding bars. The conduits of the connection branches are in communication with the inner space of the double helix or the hollow space of the casing between two adjacent vertical guiding bars. Preferably catheters are connected to the connection branches and the catheters remain in the interior space of the pot until the device is used.

In the case of a truncated pot this tapers towards the bottom.

The outer wall of the double casing is provided with a circumferentially outwardly extending ledge at the brim to accomodate a sealing sheet. The sealable sealing sheet as well as the double casing is prepared from a sterilisable material to allow the sterilisation of the device together with the connected catheters located within the pot subsequent to the application of the sealing sheet and to enable storage under these conditions till use. The catheter as well as the hollow space of the casing are sterile until used. Prior to use the sealing sheet is peeled off and the catheters are removed from the pot and one of them is connected with a source of the fluid to be tempered and the other catheter is provided with a suitable administering tip, provided such a tip had not previously been added, and stored under the sterile conditions. The interior of the pot is filled with a warm or hot liquid to adjust the temperature of the treating fluid passing through the hollow space of the casing whereby a heat exchange between the treating fluid and the liquid within the interior of the pot takes place. For cooling, preferably ice-water is filled into the pot, and for heating correspondingly hot liquids are used or liquid medium is heated by means of immersion heater or a Peltier element, and maintained at this higher temperature level.

It is an advantage of the specific structure of the device according to the invention that the device comprises only two parts of plastic which need only be inserted into each other. The catheters only have to be connected to the connection branches and be placed whithin the interior of the pot. Subsequently the device is sealed with the sealing sheet and sterilised ready for use.

Suitable polymers are polystyrene, copolymers of polystyrene, i.e. butadiene styrene copolymeres, polyamide, polycarbonates, polyurethane, copolymeres of butadiene-styrene-acrylates, graft polymers of styrene and acrylonitrile on acrylate rubber, polyolefines, polyoxymethylene resins and further polymers which can be processed by injection moulding, injection blowing or press moulding. The same plastics can be used for the outer wall and for the inner wall, whereby polyolefines such as polyethylene, polypropylene are preferred, because these polymeres allow an easier sealing of sterilisable sealing sheets. Suitable sterilisable sealing sheets can be of paper, coated paper or the ethylene non-wovens or similar materials, whereby a coating of the sheet is adapted to the polymere material of the outer wall to enable a sealable sterilisable connection between the sheet and the ledge of the outer wall.

A stable connection between the catheters and the connection branches can be realized by using an adhesive, by pressing or by welding.

The size of the double casing is such that the interior of the pot holds from 1 to 5 for cooling respectively heating liquid. The difference between the diameter of the outer wall and of the inner wall and the difference in height between outer and inner wall is selected so as to provide a hollow space within the casing having a volume of between 20 and 100 ml, preferably between 30 to 50 ml.

The inner wall as well as the outer wall of the device according to the invention can be prepared by injection moulding or injection blowing or press moulding. The outer wall could also be deep-drawn. To improve the insulation effect of the outer wall the polymer of this wall can be foamed. The manufacturing of such a foamed wall can be done by reaction injection moulding or by deep-drawing of a foamed material.

Subsequent to the assembling of the walls the catheters are placed in the interior of the pot and connected to the connecting branches by an adhesive or by welding, and the pot is sealed with a sealable sterilisable sealing sheet and, if desired, subsequently sterilised in the closed condition.

A more detailed description of the invention is given with reference to the figures.

BRIEF DESCRIPTION OF THE DRAWINGS

FIG. 1 shows one embodiment of the device according to the invention. The heat exchanger means 1 has a structure of a conically truncated double cased pot comprising an outer wall 2 and an inner wall 3 and there between the hollow space 4 of the casing. The outer wall 2 is higher than the inner wall 3, preferably about one third higher. The difference in height between the outer wall and the inner wall is sufficient for catheters to be attached to the connection branches 6, 7 and arranged in the interior 8 of the heat exchanger pot 1 without being bent. There is no point in making the difference too great since this would result in a surface area of the double casing which is too small for sufficient heat exchange. The hollow space 4 of the casing is sealed by a ledge 5 surrounding the brim of the inner wall and extending outwards to the outer wall 2 The outer wall 2 of the embodiment according to FIG. 1 comprises a pot with a shoulder round the circumference extending outwards from the outer wall 2 positioned at a distance from the base corresponding to the height of the inner wall 3. The outer diameter of the surrounding ledge at the brim of the inner wall 3 correspondes with that of the inner diameter of the outer wall 2. The construction with the step and the increased diameter of the inner wall by means of the ledge 5 results in a larger sealing surface between the two walls compared to an outer wall 2 without such a shoulder. Such an increased sealing surface is of advantage, but is not necessary in the event that the ledge 5 is sufficiently thick that the outer edge can act as a sealing surface. Instead of one ledge 5, two or more ledges running parallel to each other can be provided to seal the hollow space 4 of the casing at its upper end. Where a plurality of ledges is used and an outer wall 2 with a shoulder the ledges can join the inner surface of the outer wall 2 above wall 2 above the shoulder or partially below the shoulder. The depth of the ledges must at all events be so that they join the inner surface to the outer wall 2.

Figure 1:
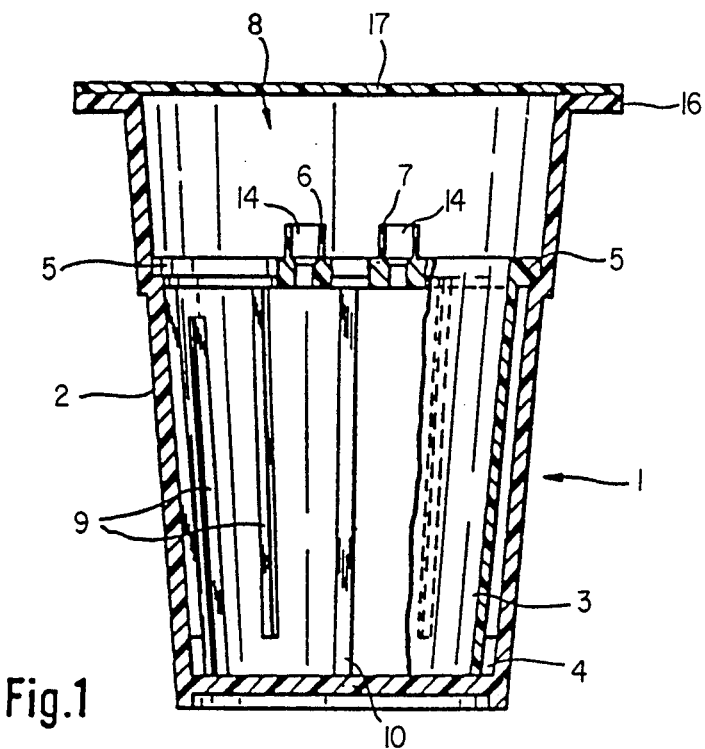
FIG. 1 is a view of one embodiment of the double cased pot having vertical guiding bars positioned within the hollow space of the casing.

Two connection branches 6, 7 are arranged along the ledge 5 both spaced apart from each other The connection branches 6, 7 extend into the interior 8 of the pot 1, and into the hollow space 4 of the double casing, whereby the conduits 14 are in communicaton with the hollow space of the casing. The connection branches 6 and 7 are located adjacent to a guiding bar 10 extending from the rim to the bottom of the hollow space 4 between the walls of the double casing. Further guiding bars 10 are alternatively arranged around the circumference of the hollow space 4 of the casing, leaving a space either from the bottom or the top of the hollow space 4, to increase the flow path of the liquid medium within the hollow space 4 of the double casing. The number of the guiding bars 10 can vary, but is preferably selected so that the distance between two adjacent guiding bars, when uniformly arranged, results in a free cross-section of the formed channel within the hollow space of the double casing of between 6.5 and 7.5 mm$^2$.

Preferably not only the inner cross-section of the conduits of the connection branches but also the free cross-section within the hollow space of the casing have approximately the same free cross-section for the fluid medium as that of the connected catheters.

The inner wall 3, in order to form double case, can be a truncated cone open both at the top and bottom which is inserted into an outer wall 2 having the form of a pot. The guiding bars 9, 10 are preferably arranged at the outer surface of the inner wall 3 and join the inner surface of the outer wall 2 In general, it is also possible for the guiding bars 9, 10 to be on the inner surface of the outer wall 2 and joining outer surface of the inner wall 3. It is also possible to provide guiding bars at the inner wall 3 as well as at the outer wall 2, i.e. the guiding bars on the outer wall 2 extend to the bottom of the pot and the guiding bars on the inner wall 3 extend to the brim of the hollow space 4 of the casing.

The surfaces of the outer edges of the guiding bars 9, 10 and of the ledge 5 can be provided with an adhesive to improve sealing, and to fasten the inner wall 3 to the outer wall 2. The dimensions of the outer wall 2, the inner wall 3, to the depth of the guiding bars 9, 10 and the ledge 5 can be constructed so that when inserted into each other the two parts result in a sealed hollow space 4 of the casing.

The outer wall 2 is provided round the circumference of its brim with a ledge 16 extending outwards to accomodate a sealing sheet 17.

Figure 2:
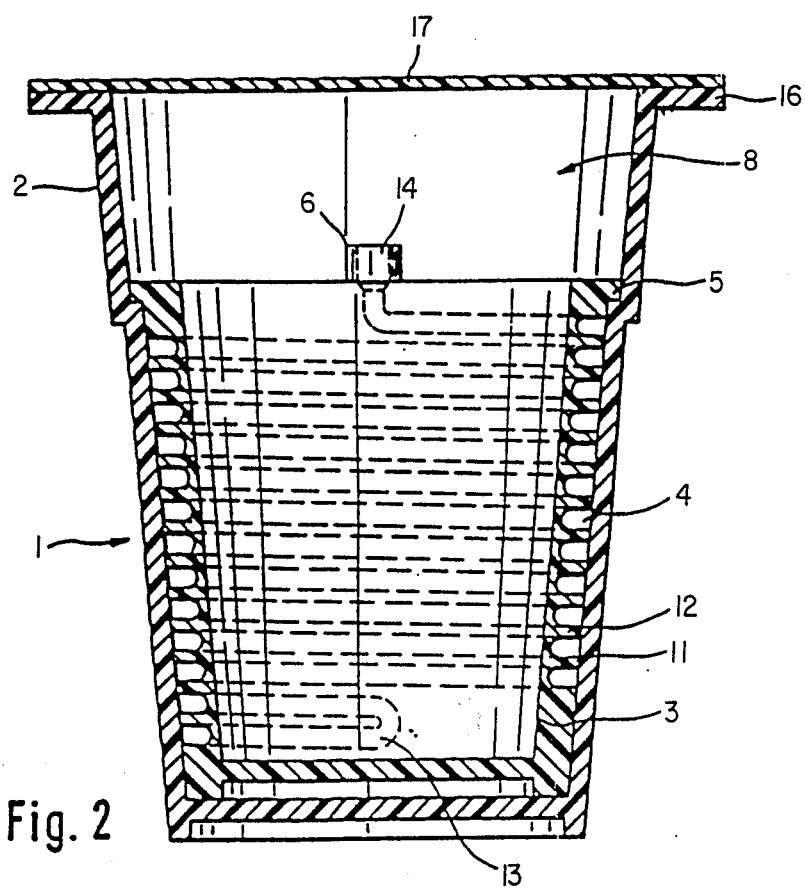
FIG. 2 is another embodiment of the double cased pot with ridges forming a double thread or a double helix positioned within the hollow space of the casing.

FIG. 2 shows another embodiment of the device according to the invention. The heat exchanger in form of a double cased pot 1 has an outer wall 2 in form of a pot tapering towards the bottom. The inner wall 3 is a shorter pot with less diameter than the outer wall 2, in order to provide a hollow space 4 between the outer wall 2 and the inner wall 3 after insertion of the inner wall into the outer wall. The hollow space 4 of the casing is sealed by a ledge 5 at the brim of the inner wall 3 extending outwards to the outer wall 2. The surface of this ledge 5 corresponds to the surface of the shoulder in the outer wall 2 positioned at the same height so that the sealing surface is increased by the width of the outwardly extending shoulder in the outer wall 2. The ledge 5 shown in FIG. 2 can be provided in the form of a plurality of ledges spaced parallel to one each other and having sufficient depth that the webs join the inner surface of the outer wall 2. For technological manufacturing reasons the pot of the inner wall 3 is provided with a projecting ridge with an outer diameter of said ledge that joins the inner surface of the outer wall 2. By such a structure the hollow space 4 of the casing between the walls of the double casing is sealed at the top as well as at the bottom. The pot of the inner wall 3 is about two third the height of the pot of the outer wall 2. The difference in height enables the catheters to be connected to the connection branches 6 and 7, which protrude from the ledge 5 into the interior 8 of the pot, and to be arranged within the interior 8 without bending. The two connection branches 6 and 7 are positioned on the ledge 5 at a distance from each other and are preferably located opposite each other. The connection branches 6 and 7 extend into the interior 8 of the pot and into the hollow space 4 of the casing, wherein the conduits 14 of the connection branches are in communication with the hollow space 4 of the casing. Instead of vertical ridges between the walls 2 and 3 of the double casing two parallel ridges 10 and 11 are provided within the double casing, occupying the whole space in the form of a double helix forming a double thread. The ends of the double helix are in communication with the connection branches 6 and 7 and the return path commences adjacent to the bottom of the pot in form of a semi-circular arch 13. The depth of the guiding bar 11 and 12, i.e. their outer diameter is selected selected in such a way that they join the inner surface of the outer wall 2. The depth of the double thread which is formed by the ridges 11 and 10 and the distance of the ridges from one another is selected so that the cross-section of the thus formed channel within the hollow space of the casing is between 6.5 and 7.5 mm$^2$. The connection branches 6 and 7 are provided with conduits 14 in the form of a so-called blind holes. The conduits have a diameter of for example 4.1 mm for the portion extending into the interior 8, and the portion extending into the hollow space of the casing has a diameter of for example 3 mm. The conduits of each of the two connection branches are in communication with each of the ends of the double thread so that one of the connection branches acts as an inlet branch for the hollow space 4 of the casing and the other acts as an outlet branch. The flow path within the hollow space of the casing first travels down the thread to the bottom of the pot, through the semi-circular arch 13 into the parallel thread travelling up to the outlet branch.

In general it is possible to provide a structure of the inner wall 3 as a casing open at the bottom instead of as a pot. In such an event the double helix is positioned at the outer surface of the inner wall 3 in a similar manner, and the sealing at the bottom is achieved by a ridge of thicker material at the lower end of the wall 3.

In general it is possible to form the channel within the double casing by providing ridges in the form of a double thread or a double helix at the inner surface of the outer wall 2, and by inserting an inner wall 3 with a smooth outer surface, thus joining the ridgesg bars and forming a sealed hollow space in the casing. In such an event it is of advantage, however, to provide the inner wall 3 with the ledge 5 at its brim for the sealing of the hollow space 4 of the casing, from which the connection branches 6 and 7 protrude.

For technical reasons, a truncated conical form of the outer wall 2 as well as the inner wall 3 is preferred to a hollow cylindrical structure of the walls.

The outer wall 2 is provided with a ledge 16 at the brim which extends outwards to accomodate a sealing sheet 17. The flange 16 can have a circular notch to assist the peeling off of a fixed sealing sheet 17. In the event that there is no notch the sealing sheet should have a tongue to facilitate the peeling off.

Figure 3:
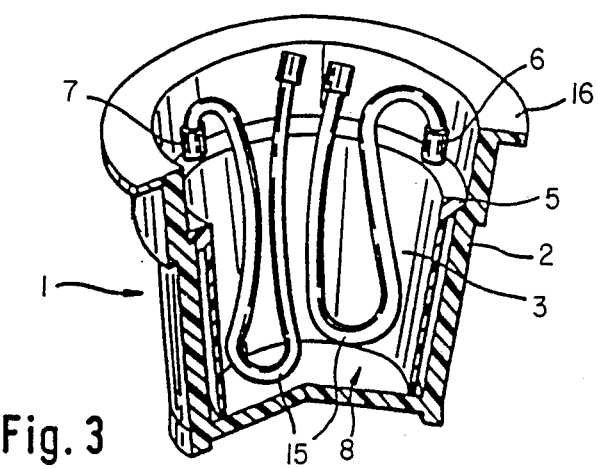
FIG. 3 is a partial cut view of one embodiment of the double cased pot with catheters connected to the connection branches and arranged in the pot.

FIG. 3 shows a cut section diagram of one embodiment of the double casing pot 1 according to the invention having an outer wall 2 and an inner wall 3. This embodiment of the invention has a thicker wall 2 than the inner wall 3 to improve the insulating effect.

In such an event the outer wall is preferably formed from foamed plastic. The outer wall 2 is higher than the inner wall 3 and the outer wall has an outwardly extending ledge 16 at its brim. Connection branches 6 and 7 protrude from the sealing ledge 5 to the hollow space 4 of the casing at its upper end, into the interior 8 of the pot. Catheters 15 are attached to these connection branches, and are arranged in the interior 8. The free ends of the catheters are preferably provided with so-called Luer connections. These are truncated connection members according to DIN 13090.

Figure 4:
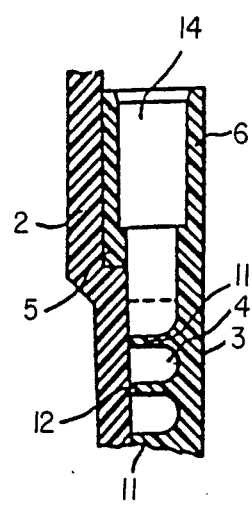
FIG. 4 is an enlarged cross-section showing in detail the arrangement of the outer wall and the inner wall where one of the connection branches enters.

FIG. 4 is an enlarged detail of the structure at the upper end of the inner wall 3 and its relation to the outer wall 3. The inner wall 3 has an outwardly surrounding edge at its brim, the outer diameter of which corresponds to the inner diameter of the outer wall 2 above the outwardly extending shoulder. The under side of said ledge 5 joins the upper surface of the shoulder at the outer wall 2. The connection branch 6, protruding from said ledge 5 is provided with a conduit 14 in the form of a blind hole connected to the thread of the double helix within the hollow space 4 of the casing. The double helix of the double thread within the hollow space 4 of the casing is formed by parallel extending ridges 11 and 12. The outer edges of the ridges 11 and 12 join the inner surface of the outer wall 2.

A sealing connection of the joining surfaces can be obtained with an adhesive or by shrinkage of the outer wall 2 on to the inner wall 3. This can be realized by inserting a preformed cooled inner wall 3 into a hot outer wall 2, which is stable in its form, and cooling to room temperature causing a shrinkage of the outer wall 2 and resulting in a rigid fit and connection of both parts. Shrinking is preferred to the use of adhesives because this method is less complicated.

EXAMPLE

The embodiment shown in FIGS. 2 and 4 of the double cased pot according to the invention can have the following size:

Height of the outer wall of the pot 133 mm.
Outer diameter of the outwardly extending upper ledge of the outer wall 130 mm.
Inner diameter of the outer wall at the upper ledge 104 mm,
Distance between the shoulder of the outer wall and the upper edge 53 mm,
Inner diameter of the outer wall at the shoulder 99.9 mm.
Height of the inner wall 81 mm.
Inner diameter of the outer wall at the bottom 89.9 mm,
Depth of the double thread 3 mm and
Distance between the threads 3 mm.
Interior volume of the double casing 30 ml,
Diameter of the conduit of the connection branch min. 3 mm and max. 4.1 mm.
Height of the connection branch 7.5 mm and
Outer diameter of the connection branch 5.8 mm.

What is claimed is:

1. A device for heating or cooling infusion fluids or injectable fluids comprising a heat exchanger in the form of a hollow cylindrical or truncated conical pot, open at the top, characterized in that the pot has a double casing and the outer wall of the pot is higher than the inner wall of the double casing whereby the hollow space of the casing is sealed by a ledge surrounding the brim of the inner wall and extending outwardly to the outer wall and the ledge is provided with two connection branches, one branch for the inlet of said infusion fluids or injectable fluids to be cooled or heated and the other branch for the outlet of said infusion fluids or injectable fluids after being cooled or heated, spaced apart from each other and extending within the inner space of the pot and below the brim of the outer wall of said pot, said outer wall is further provided with a circumferentially outwardly extending ledge at the brim to accommodate a sealing sheet.

2. The device of claim 1, wherein vertical guiding bars are positioned around the circumference of the hollow space between said inner and outer walls alternatively leaving a space from the bottom and the top of the hollow space with the connection branches being positioned at each side and spaced apart from the guiding bar extending from the bottom to the top of the hollow space of the casing and also being spaced apart from each of the adjacent vertical guiding bars.

3. The device of claim 2 wherein the inner wall of the double casing is a pot and from the outer surface of which the ledge at the brim as well as the guiding bars project to such an extent that they fit tightly against the inner surface of the outer wall.

4. The device of claim 1 further comprising catheters which are attached to the connection branches which are positioned within the interior of the double cased pot.

5. The device of claim 1, wherein two parallel guiding bars in the form of a double helix, forming a double thread, completely occupying the hollow space of the casing between the inner and outer walls wherein each of the ends of the double helix is connected to one of the connection branches and the return way of the double helix is located close to the bottom of the pot as a semi-circular arch.

6. A device for heating or cooling infusion fluids or injectable fluids comprising a heat exchanger in the form of a hollow cylindrical or truncated conical pot, open at the top, characterized in that the pot has a double casing and the outer wall of the pot is higher than the inner wall of the double casing whereby the hollow space of the casing is sealed by a ledge surrounding the brim of the inner wall and extending outwardly to the outer wall and the ledge is provided with two connection branches, one branch for the inlet of said infusion fluids or injectable fluids to be cooled or heated and the other branch for the outlet of said infusion fluids or injectable fluids after being cooled or heated, spaced apart from each other and extending within the inner space of the pot and below the brim of the outer wall of said pot and two parallel guiding bars in the form of a double helix, forming a double thread, completely occupying the hollow space of the casing between the inner and outer walls wherein each of the ends of the double helix is connected to one of the connection branches and the return way of the double helix is located close to the bottom of the pot as a semi-circular arch.

7. The device of claim 6 wherein the connection branches protrude upwards from the ledge and extend into the hollow space of the casing to each of the termination portions of the double helix and the inner conduits of the connection branches communicate with the inner space of the double helix.

8. The device of claim 6 wherein the outer wall is provided with circumferentially outwardly extending ledge at the brim to accommodate a sealing sheet.

9. The device of claim 8 wherein the pot is sealed with a sterilisable sealing sheet at its ledge.

* * * * *